United States Patent

Cannady et al.

[11] Patent Number: 5,872,274
[45] Date of Patent: Feb. 16, 1999

[54] METHOD FOR PREPARATION OF TERTIARY-HYDROCARBYLSILYL COMPOUNDS

[75] Inventors: John Patrick Cannady; Binh Thanh Nguyen, both of Midland, Mich.

[73] Assignee: Dow Corning Corporation, Midland, Mich.

[21] Appl. No.: 96,324

[22] Filed: Jun. 11, 1998

[51] Int. Cl.$^6$ .................................................. C07F 7/08
[52] U.S. Cl. ............................................................ 556/480
[58] Field of Search ............................................... 556/480

[56] References Cited

U.S. PATENT DOCUMENTS

| | | | |
|---|---|---|---|
| 2,902,504 | 9/1959 | Nitzsche et al. | 556/480 |
| 5,068,386 | 11/1991 | Shirahata | 556/480 |
| 5,294,727 | 3/1994 | Kubota et al. | 556/480 |
| 5,629,439 | 5/1997 | Nank et al. | 556/480 |
| 5,756,796 | 5/1998 | Davern et al. | 556/480 |

*Primary Examiner*—Paul F. Shaver
*Attorney, Agent, or Firm*—Melvin D. Fletcher

[57] ABSTRACT

A method for the preparation of tertiary-hydrocarbylsilyl compounds. The method comprises contacting a mixture comprising diethylene glycol dibutyl ether, and a Grignard reagent described by formula RMgX with a silicon compound described by formula $R^1{}_a SiX_{4-a}$, where R is a tertiary-hydrocarbyl group comprising four to about 20 carbon atoms, each $R^1$ is an independently selected substituted or unsubstituted monovalent hydrocarbon group comprising one to about 20 carbon atoms, each X is an independently selected halogen atom, and a is an integer with a value of zero to three, in the presence of an effective amount of a copper compound catalyst. The present invention provides a method for making sterically hindered organosilicon intermediates useful in the pharmaceutical industry.

10 Claims, No Drawings

5,872,274

1

METHOD FOR PREPARATION OF TERTIARY-HYDROCARBYLSILYL COMPOUNDS

BACKGROUND OF INVENTION

The present invention is a method for the preparation of tertiary-hydrocarbylsilyl compounds. The method comprises contacting a mixture comprising diethylene glycol dibutyl ether, and a Grignard reagent comprising a tertiary-hydrocarbylsilyl group with a silicon compound in the presence of a copper compound. The present invention provides a method for making sterically hindered organosilicon intermediates useful in the pharmaceutical industry.

It is known that copper cyanide as a catalyst in tetrahydrofuran or diethyl ether may be used to prepare sterically hindered tertiary-hydrocarbylsily compounds. However copper cyanide is a known irritant that is highly toxic and presents several environmental hazards.

Shirahata, U.S. Pat. No. 5,068,386, teaches a method for the preparation of tert-hydrocarbylsilyl compounds by reacting a Grignard reagent with a silicon compound in the presence of a cyano compound or a thiocyanate compound. The major drawback with this method is that the catalysts used are highly toxic and are irritants.

Kubota et al., U.S. Pat. No. 5,294,727, teach a method for preparing a tertiary hydrocarbon-silyl compound prepared by reacting a hydrogen halogenosilane, in which hydrogen and halogen atoms are directly bonded to the silicon atom, with a tertiary alkyl Grignard reagent in the presence of a copper compound and/or a quaternary ammonium salt. This method is to preparing the less sterically hindered Si-H containing chlorosilanes.

The present invention provides a method for preparing highly sterically hindered tertiary-hydrocarbylsilyl compounds using a Grignard reagent in the presence of a copper compound avoiding many of the above discussed problems. In addition, the method provides for a two-phase system from which the tertiary-hydrocarbylsilyl compound can be easily separated. Furthermore, the present method provides a substantial reduction in the amount of solvent used and increases the production equipment volumetric efficiency resulting in decreased production cost. The tertiary-hydrocarbylsilyl compounds prepared by the present method are useful, for example, as intermediates in the preparation of silylating agents, steroids and prostaglandins.

SUMMARY OF INVENTION

The present invention is a method for the preparation of tertiary-hydrocarbylsilyl compounds. The method comprises contacting a mixture comprising diethylene glycol dibutyl ether, and a Grignard reagent comprising a tertiary-hydrocarbylsilyl group with a silicon compound in the presence of a copper compound. The present invention provides a method for making sterically hindered organosilicon intermediates useful in the pharmaceutical industry.

DESCRIPTION OF INVENTION

The present invention is a method for the preparation of tertiary-hydrocarbylsilyl compounds. The method comprises contacting a mixture comprising diethylene glycol dibutyl ether, and a Grignard reagent described by formula RMgX with a silicon compound described by formula $R^1_a SiX_{4-a}$, where R is a tertiary-hydrocarbyl group comprising four to about 20 carbon atoms, each $R^1$ is an independently selected substituted or unsubstituted monovalent hydrocarbon group comprising one to about 20 carbon atoms, each X is an independently selected halogen atom and a is an integer with a value of zero to three, in the presence of an effective amount of a copper compound catalyst.

Contacting of the mixture comprising diethylene glycol dibutyl ether (DEGDBE) and the Grignard reagent with a silicon compound can be effected in standard reactors suitable for running Grignard type reactions. The reactor can be of a batch-type, semi-batch type, or continuous-type. The preferred reactor is a semi-batch type reactor. The environment in which the present method is run should be inert. Therefore, in a preferred method the reactor is purged and blanketed with an inert gas such as, for example, nitrogen or argon.

The Grignard reagents useful in the method are described by formula the RMgX, where R is a tertiary-hydrocarbyl group comprising four to about 20 carbon atoms and X is a halogen atom such as chlorine or bromine. R can be, for example, a tertiary-hydrocarbyl group such as tert-butyl, 1,1-dimethylpropyl, and 1,1-diethylpropyl; and an aryl substituted group such as 1,1-dimethyl-2-phenylethyl, and 1,1-dimethylbenzyl. Specific examples of Grignard reagents useful in the method include t-butyl magnesium chloride, t-butyl magnesium bromine, 1,1-dimethylpropyl magnesium chloride, 1,1-diethylpropyl magnesium chloride, 1,1-dimethyl-2-phenylethyl magnesium chloride, and 1,1-dimethylbenzyl magnesium chloride.

The Grignard reagents comprising a tertiary-hydrocarbyl group can be prepared by reacting magnesium metal with a tertiary-halide in the presence of DEGDBE. The method of preparing the magnesium metal and the physical form of the magnesium metal can be any of those known in the art. The magnesium metal can be, for example, in powder, chips or turning form. The preferred form of magnesium metal is turnings.

In an alternative embodiment of the present method, the tertiary-hydrocarbylsilyl compounds may be made "in situ". By the term "in situ" it is meant that it is not necessary to isolate an intermediate Grignard reagent prepared by reacting magnesium metal with a tertiary-halide in the presence of DEGDBE and then reacting this Grignard reagent with the silicon compound in the presence of the copper compound. In the method, the reactor may be loaded with a tertiary-halide, DEGDBE, magnesium metal, and silicon compound in the presence of a copper compound all in one step.

The mole ratio of magnesium metal to tertiary-halide fed to the reactor is not critical and can be varied within wide limits. In a batch method it is preferred that the mole ratio of magnesium metal to tertiary-halide provide tertiary-halide in sufficient excess to ensure essentially total conversion of the magnesium metal to Grignard reagent. When the method is conducted as a semi-batch, the magnesium metal is typically present in excess in relation to the tertiary-halide fed to the reactor.

The use of DEGDBE as a solvent as compared to other ether-type organic solvents results in a substantial reduction in the amount of solvent used and increases the production equipment volumetric efficiency resulting in decreased production cost. In the method 0.01 to about 15 moles of DEGDBE can be added per mole of silicon compound. Preferred is when 0.1 to about 10 moles of DEGDBE is added per mole of silicon compound. Even more preferred is when 0.5 to about 2 moles of DEGDBE is added per mole of silicon compound.

The silicon compounds useful in the present method are described by formula $R^1_a SiX_{4-a}$, where $R^1$ is a substituted or unsubstituted monovalent hydrocarbon group comprising one to about 20 carbon atoms, X is as previously defined and a is an integer with a value of zero to three. $R^1$ can be alkyl groups such as methyl, ethyl, propyl, n-propyl, butyl, t-butyl, pentyl, hexyl, heptyl, octyl, nonyl, decyl, undecyl, and dodecyl; a cycloalkyl such as cyclopropyl, cyclobutyl, cyclopentyl, cyclohexyl, cycloheptyl, and cyclooctyl; an alkenyl group such as vinyl, allyl, and hexenyl; a cycloalkenyl such as cyclobutenyl, cyclopentenyl and cyclohexenyl; an aryl group such as phenyl, tolyl, and naphthyl; an arylalkyl such as benzyl, and beta-phenylethyl. Preferred is when a is 1 or 2 and $R^1$ is methyl. Specific examples of silicon compounds are methyltrichlorosilane, tetrachlorosilane, phenyltrichlorosilane, dichlorosilane, diphenyldichlorosilane, vinyltrichlorosilane, n-propyltrichlorosilane, t-butyldimethylchlorosilane, vinylmethyldichlorosilane, n-propyltrichlorosilane, and allyltrichlorosilane.

The copper compounds useful in the present method as catalyst are selected from the group consisting of cupric chloride, cuprous chloride, copper nitrate, copper sulphate, copper cyanide, copper thiocyanate, copper acetate, copper fluoride, copper bromide, copper methoxide and copper hydroxide. These copper compounds may be used alone or in any combination.

An effective amount of copper compound used in the present method is any amount that affects the conversion rate of Grignard reagent to tertiary-hydrocarbylsilyl compounds. The amount of the copper compound used can range from about 0.01 to 10 mole percent per the moles of the silicon compound. Preferably the amount of the copper compound used ranges from about 0.1 to 5 mole percent per the moles of the silicon compound.

The present method can be run at a temperature within a range of about 5° C. to 200° C. It is preferred that the method be run at a temperature within a range of about 30° C. to 170° C. Most preferred is when the method is conducted at a temperature within a range of about 80° C. to 100° C. The pressure at which the method is run is not critical and can be atmospheric to about 1480 kPa, however it is preferred that the pressure be at or above the vapor pressure of the reaction mixture. A preferred pressure is within a range of from atmospheric to about 963 kPa.

The product of the present method is a tertiary-hydrocarbylsilyl compound, where the tert-hydrocarbyl group originating with the starting Grignard reagent will be present in the final compound bonded directly to the silicon atom. The three remaining substituents on the silicon atom are exemplified by halogen atoms and/or substitued or unsubstituted monovalent hydrocarbon groups. Examples of tertiary-hydrocarbylsilyl compounds prepared by the present method include, tert-butyldimethylchlorosilane, tert-butyldiphenylchlorosilane, tert-butylmethyldichlorosilane, tert-butylmethylphenylchlorosilane, vinyltert-butyldichlorosilane, tert-butyltrichlorosilane, 1,1-dimethylbenzyldimethylchlorosilane, 1,1-dimethylbenzylmethyldichlorosilane, 1,1-dimethylpropyldimethylchlorosilane, 1,1-dimethylpropylmethyldichlorosilane, and 1,1-dimethylpropyltrichlorosilane.

The mixture resulting from conduct of the present method on standing separates into two-phases, with one phase comprising the tertiary-hydrocarbylsilyl compound in DEGDBE and the other phase comprising a magnesium dihalide complex solubilized in DEGDBE. The tertiary-hydrocarbylsilyl compound can be separated from the DEGDBE by, for example, distillation. The DEGDBE may be recovered from one or both phases and recycled to the method.

The following examples are provided to illustrate the present invention. The examples are not intended to limit the scope of the claims herein.

Example 1. Preparation of (t-butyl)(n-propyl)dichlorosilane without a catalyst. Magnesium turnings (0.79 mol) and diethylene glycol dibutyl ether (DEGDBE) (1.62 mol) were loaded into a glass flask equipped with a reflux condenser, addition funnel, mechanical stirrer, heating mantle, and nitrogen inlet port. Approximately 10 ml solution of t-butyl magnesium chloride in DEGDBE was added to the mixture comprising magnesium turnings in DEGDBE to activate the magnesium turnings. The flask was purged with nitrogen and then heated to 65° C. for 2 hours. t-Butylchloride (0.77 mol) was added dropwise to the mixture in the flask and within 13 minutes the mixture temperature reached 113° C. After 23 minutes the temperature decreased to 63° C. and addition of t-butylchloride continued for about 30 minutes until the magnesium was consumed. The mixture was analyzed by gas chromatography using a flame ionization detector (GC-FID) and found to be t-butylmagnesium chloride.

n-Propyltrichlorosilane (0.30 mol) and approximately 150 ml of t-butylmagnesium chloride in DEGDBE prepared above were loaded into a flask. No reaction appeared to occurred immediately, and the flask contents were allowed to mix for about 12 hours. A sample analyzed by GC-FID indicated the presence of trace amounts of (t-butyl)(n-propyl)hydrochlorosilane and (t-butyl)(n-propyl)dichlorosilane.

Example 2. Preparation of (t-butyl)(n-propyl)dichlorosilane with copper thiocyanate as catalyst. Copper thiocyanate (0.12 g) and n-propyltrichlorosilane (0.30 mol) were loaded into a flask. The temperature of the flask content was maintained at about 67° C. as t-butylmagnesium chloride in DEGDBE (150 ml) prepared as in example 1 was added to the flask. A two phase solution formed instantly. GC-FID analysis indicated that top phase contained 50.0 wt % DEGDBE, 37.8 wt % unreacted n-propyltrichlorosilane, 6.2 wt % (t-butyl)(n-propyl)dichlorosilane and 0.5 wt % (t-butoxy)(n-propyl)dichlorosilane.

Example 3. Preparation of (t-butyl)(n-propyl)dichlorosilane with copper acetate as catalyst. Copper acetate (0.041 g) and n-propyltrichlorosilane (0.41 mol) were loaded into a flask. The temperature of the flask content was maintained at about 22° C. as t-butylmagnesium chloride in DEGDBE solution (150 ml) prepared as in example 1 was added to the flask. A two phase solution formed instantly and after about 12 minutes turned colorless. GC-FID analysis indicated that the top phase contained 65.2 wt % DEGDBE, 25.2 wt % unreacted n-propyltrichlorosilane, 3.4 wt % (t-butyl)(n-propyl)dichlorosilane and 0.8 wt % (t-butoxy)(n-propyl)dichlorosilane.

Example 4. Preparation of (t-butyl)(n-propyl)dichlorosilane prepared with copper sulfate as catalyst. Copper sulfate (0.054 g) and n-propyltrichlorosilane (0.28 mol) were loaded into a flask. The temperature of the flask content was maintained at about 22° C. as t-butylmagnesium chloride in DEGDBE solution (75 ml) prepared as in example 1 was added to the flask. A two phase solution formed. GC-FID analysis indicated the top phase contained 65.5 wt % DEGDBE, 26 wt % unreacted n-propyltrichlorosilane, 7.7 wt % (t-butyl)(n-propyl) dichlorosilane and 0.8 wt % (t-butoxy)(n-propyl) dichlorosilane.

Example 5. Preparation of (t-butyl)(n-propyl) dichlorosilane with cuprous chloride (Cu(I)Cl) as catalyst. Cuprous chloride (0.082 g) and n-propyltrichlorosilane (0.31 mol) were loaded into a flask. The temperature of the flask content was maintained at 22° C. as t-butylmagnesium chloride in DEGDBE solution (150 ml) prepared as in example 1 was added to the flask. A two phase solution formed within 5 minutes. GC-FID analysis indicated that the top phase contained 61.2 wt % DEGDBE, 28.4 wt % unreacted n-propyltrichlorosilane, 6.5 wt % (t-butyl)(n-propyl)dichlorosilane and 0.4 wt % (t-butoxy)(n-propyl) dichlorosilane.

Example 6. Preparation of (t-butyl)(n-propyl) dichlorosilane with cupric chloride (Cu(II)Cl) as catalyst. Cupric chloride (0.07 g) and n-propyltrichlorosilane (0.36 mol) were loaded into a flask. The temperature of the flask content was maintained at 22° C. as t-butylmagnesium chloride in DEGDBE solution (168 g) prepared as in example 1 was added to the flask. A two phase solution formed within 5 minutes. GC-FID analysis indicated that the top phase contained 78.4 wt % DEGDBE, 0 wt % unreacted n-propyltrichlorosilane, 17.9 wt % (t-butyl)(n-propyl) dichlorosilane and 0.6 wt % (t-butoxy)(n-propyl) dichlorosilane.

Example 7. Preparation of (t-butyl)(n-propyl) dichlorosilane with copper nitrate ($Cu(NO_3)_2$) as catalyst. Copper nitrate (0.06 g) and n-propyltrichlorosilane (0.35 mol) were loaded into a flask. The temperature of the flask content was maintained at about 22° C. as t-butylmagnesium chloride in DEGDBE solution (165 g ) prepared as in example 1 was added to the flask. A two phase solution formed within 5 minutes. GC-FID analysis indicated that the top phase contained 64.2 wt % DEGDBE, 15.9 wt % unreacted n-propyltrichlorosilane, 16.0 wt % (t-butyl)(n-propyl)dichlorosilane and 0.1 wt % (t-butoxy)(n-propyl) dichlorosilane.

Example 8. Preparation of (t-butyl)(n-propyl) dichlorosilane with copper methoxide as catalyst. Copper methoxide (0.1 g) and n-propyltrichlorosilane (0.36 mol) were loaded into a flask. The temperature of the flask content was maintained at about 22° C. as t-butylmagnesium chloride in DEGDBE solution (166 g) prepared as in example 1 was added to the flask. A two phase solution formed within 5 minutes. GC-FID analysis indicated that the top phase contained 75.7 wt % DEGDBE, 0% unreacted n-propyltrichlorosilane, 19.3 wt % (t-butyl)(n-propyl) dichlorosilane and 0.8 wt % (t-butoxy)(n-propyl) dichlorosilane.

Example 9. Preparation of (t-butyl)(n-propyl) dichlorosilane with copper hydroxide as catalyst. Copper hydroxide (0.1 g) and n-propyltrichlorosilane (0.36 mol) were loaded into a flask. The temperature of the flask content was maintained at about 22° C. as t-butylmagnesium chloride in DEGDBE solution (163.5 g) prepared as in example 1 was added to the flask. A two phase solution formed within 5 minutes. GC-FID analysis indicated that the top phase contained 39.9 wt % DEGDBE, 13.2 wt % unreacted n-propyltrichlorosilane, 28.2 wt % (t-butyl)(n-propyl) dichlorosilane and 1.2 wt % (t-butoxy)(n-propyl) dichlorosilane.

Example 10. Preparation of t-butyldimethylchlorosilane without a catalyst. Dimethyldichlorosilane (0.6 mol) and 150 ml of t-butylmagnesium chloride in DEGDBE prepared as in example 1 were loaded into a flask. No reaction appeared to occurred after 18 hours at 23° C. The flask contents were allowed to mix for an additional 4 hour at 65° C. and there still appeared to be no reaction. A sample was analyzed by GC-FID indicated trace amounts of t-butyldimethylchlorosilane.

Example 11. Preparation of t-butyldimethylchlorosilane with copper acetate as catalyst. Copper acetate (1.0 g) and dimethyldichlorosilane (0.72 mol) were loaded into a flask. The temperature of the flask content was maintained at 50° C. as t-butylmagnesium chloride in DEGDBE solution (150 ml) prepared as in example 1 was added to the flask. Within 5 minutes the mixture formed a liquid top gray phase and a liquid bottom black phase. After 10 minutes the liquid top phase became colorless. GC-FID analysis indicated that the colorless top phase contained 15.4 wt % t-butyldimethylchlorosilane, 24.0 wt % dimethyldichlorosilane and 39.5 wt % DEGDBE.

Example 12. Preparation of t-butyldimethylchlorosilane with copper cyanide as catalyst. Copper cyanide (0.7 g) and dimethyldichlorosilane (0.6 mol) were loaded into a flask. The temperature of the flask content was maintained at 23° C. as t-butylmagnesium chloride in DEGDBE solution (100 ml) prepared as in example 1 was added to the flask. Within 5 minutes the mixture formed a liquid top yellow phase and a liquid bottom black phase. GC-FID analysis indicated that the top phase contained 16.9 wt % t-butyldimethylchlorosilane, 28.3 wt % dimethyldichlorosilane and 48.5 wt % DEGDBE.

Example 13. Preparation of t-butyldimethylchlorosilane with cuprous chloride as catalyst. Cuprous chloride (0.7 g) and dimethyldichlorosilane (0.7 mol) were loaded into a flask. The temperature of the flask content was maintained at 23° C. as t-butylmagnesium chloride in DEGDBE solution (100 ml) prepared as in example 1 was added to the flask. Within 5 minutes the mixture formed a liquid top colorless phase and a liquid bottom black phase. GC-FID analysis indicated that the top phase contained 10.7 wt % t-butyldimethylchlorosilane, 27.1 wt % dimethyldichlorosilane and 43.0 wt % DEGDBE.

Example 14. Preparation of t-butyldimethylchlorosilane with copper nitrate as catalyst. Copper nitrate (0.62 g) and dimethyldichlorosilane (0.62 mol) were loaded into a flask. The temperature of the flask content was maintained at 23° C. as t-butylmagnesium chloride in DEGDBE solution (100 ml) prepared as in example 1 was added to the flask. Within 5 minutes the mixture formed a liquid top yellow phase and a liquid bottom black phase. GC-FID analysis indicated that the top phase contained 17.0 wt % t-butyldimethylchlorosilane, 12.7 wt % dimethyldichlorosilane and 45.8 wt % DEGDBE.

Example 15. Preparation of t-butyldimethylchlorosilane with copper sulphate as catalyst. Copper sulphate (0.62 g) and dimethyldichlorosilane (0.62 mol) were loaded into a flask. The temperature of the flask content was maintained at 23° C. as t-butylmagnesium chloride in DEGDBE solution (100 ml) prepared as in example 1 was added to the flask. Within 5 minutes the mixture formed a liquid top colorless phase and a liquid bottom black phase. GC-FID analysis indicated that the top phase contained 21.1 wt % t-butyldimethylchlorosilane, 14.4 wt % dimethyldichlorosilane and 44.1. wt % DEGDBE.

Example 16. Preparation of t-butyldimethylchlorosilane with copper hydroxide as catalyst. Copper hydroxide (0.62 g) and dimethyldichlorosilane (0.62 mol) were loaded into a glass flask equipped with a reflux condenser, addition funnel, mechanical stirrer, heating mantle, and nitrogen inlet port. The temperature of the flask content was maintained at 23° C. as t-butylmagnesium chloride in DEGDBE solution (100 ml) prepared as in example 1 was added to the flask. Within 5 minutes the mixture formed a liquid top colorless phase and a liquid bottom yellow phase. GC-FID analysis indicated the top phase contained 17.7 wt % t-butyldimethylchlorosilane, 20.2 wt % dimethyldichlorosilane and 43.0 wt % DEGDBE.

Example 17. Preparation of (t-butyl)(n-propyl) dichlorosilane prepared in situ with copper cyanide as catalyst. A mixture comprising DEGDBE (0.5 mol), magnesium turnings (0.73 mol), copper cyanide (0.0034 mol), and n-propyltrichlorosilane (0.72 mol) was loaded into a glass flask equipped with a reflux condenser, addition funnel, mechanical stirrer, heating mantle, and nitrogen inlet port. t-Butylmagnesium chloride in DEGDBE (12 ml) was added to activate the magnesium turnings. The mixture was heated to 85° C. and after one hour the t-butyl chloride (1.1 mol) was added to the mixture. Thirty minutes after the t-butyl chloride was added to the mixture over 4.5 hours period, it exothermed and the temperature increased to 118° C. DEGDBE (1.1 moles) was added to the reaction mixture and quickly absorbed the heat. GC-FID analysis of the mixture indicated 5.4 wt % (t-butyl)(n-propyl) dichlorosilane, 0.5 wt % (t-butyl)(n-propyl)chlorosilane, and 0.14 wt. % (t-butoxy)(n-propyl)dichlorosilane. The percent conversion of n-propyltrichlorosilane was 17.2% (t-butyl)(n-propyl)chlorosilane, 1.2%, (t-butyl)(n-propyl) chlorosilane, and 0.4% (t-butoxy)(n-propyl)dichlorosilane.

Example 18. Preparation of (t-butyl)(n-propyl) dichlorosilane in situ with cupric chloride as catalyst. A mixture comprising DEGDBE (0.45 mol), magnesium turnings (1.0 mol), cupric chloride (0.12 g), and n-propyltrichlorosilane (1.0 mol) was loaded into a glass flask equipped with a reflux condenser, addition funnel, mechanical stirrer, heating mantle, and nitrogen inlet port. A solution of DEGDBE (1.05 mol) and t-butyl chloride (1.41 mol) was prepared in a 1 liter bottle. The t-butylmagnesium chloride in DEGDBE (12.0 ml) was pumped into the mixture in the flask to activate the magnesium turnings and heated to 80° C. for one hour. The t-butyl chloride was added to the mixture over a three hour period. The maximum exotherm observed was 117° C., and 10 minutes later the t-butylmagnesium chloride addition started. GC-FID analysis of the mixture indicated 4.4 wt % (t-butyl)(n-propyl) dichlorosilane, and 3.6 wt % (t-butyl)(n-propyl) chlorosilane.

Example 19. Preparation of (t-butyl)(n-propyl) dichlorosilane in situ with cuprous chloride as catalyst. A mixture comprising DEGDBE (0.40 mol), magnesium turnings (1.0 mol), copprous chloride (0.2 g), and n-propyltrichlorosilane (1.0 mol) was loaded into a glass flask equipped with a reflux condenser, addition funnel, mechanical stirrer, heating mantle, and nitrogen inlet port. A solution of DEGDBE (1.4 mol) and t-butylmagnesium chloride (1.5 mol) was prepared in a 1 liter bottle. The t-butylmagnesium chloride in DEGDBE (13 ml) was pumped into the mixture in the flask to activate the magnesium turnings and heated to 80° C. for ¾ hours. The t-butyl chloride was added to the mixture over a 8 hour period. The maximum exotherm observed was 140° C. GC-FID analysis of the mixture indicated 4.4 wt % (t-butyl)(n-propyl) dichlorosilane, 0.07 wt % (t-butyl)(n-propyl)dichlorosilane, 0.1 wt % (t-butoxy)(n-propyl)dichlorosilane and 6.4 wt % DEGDBE.

Example 20. Preparation of (t-butyl)(n-propyl) dichlorosilane in situ with copper acetate as catalyst. A mixture comprising DEGDBE (0.40 mol), magnesium turnings (1.0 mol), copper acetate (1.0 g), and n-propyltrichlorosilane (1.0 mol) was loaded into a glass flask equipped with a reflux condenser, addition funnel, mechanical stirrer, heating mantle, and nitrogen inlet port. A solution of DEGDBE (1.0 mol) and t-butylmagnesium chloride (125.0 g) was prepared in a 1 liter bottle. The t-butylmagnesium chloride in DEGDBE (13 ml) was pumped into the mixture in the flask to activate the magnesium turnings and heated to 80° C. for ¾ hours. The t-butyl chloride was added to the mixture over a 5 hour period. Additional copper acetate (0.7 g) was added to the mixture. GC analysis of the mixture indicated 12.5 wt % (t-butyl)(n-propyl)dichlorosilane, 1.6 wt % (t-butyl)(n-propyl) chlorosilane, and 0.04 wt % (t-butoxy)(n-propyl) dichlorosilane.

We claim:

1. A method for preparation of tertiary-hydrocarbylsilyl compounds, the method comprising contacting a mixture comprising diethylene glycol dibutyl ether, and a Grignard reagent described by formula RMgX, with a silicon compound described by formula $R^1_a SiX_{4-a}$, where R is a tertiary-hydrocarbyl group comprising four to about 20 carbon atoms, each $R^1$ is an independently selected substituted or unsubstituted monovalent hydrocarbon group comprising one to about 20 carbon atoms, each X is an independently selected halogen atom, and a is an integer with a value of zero to three; in the presence of an effective amount of a copper compound catalyst.

2. A method according to claim 1, where $R^1$ is methyl and a is 2.

3. A method according to claim 1, where $R^1$ is n-propyl and a is 1.

4. A method according to claim 1, where $R^1$ is t-butyl and a is 1.

5. A method according to claim 1, where the copper compound catalyst is selected from the group consisting of cupric chloride, cuprous chloride, copper nitrate, copper sulphate, copper cyanide, copper thiocyanate, copper acetate, copper fluoride, copper bromide, copper methoxide and copper hydroxide.

6. A method for preparation of tertiary-hydrocarbylsilyl compounds, the method comprising contacting magnesium metal with a mixture comprising diethylene glycol dibutyl ether, a Grignard reagent described by formula RMgX, and a silicon compound described by formula $R^1_a SiX_{4-a}$, where R is a tertiary-hydrocarbyl group comprising four to about 20 carbon atoms, each $R^1$ is an independently selected substituted or unsubstituted monovalent hydrocarbon group comprising one to about 20 carbon atoms, each X is an independently selected halogen atom, and a is an integer with a value of zero to three; in the presence of an effective amount of copper compound catalyst selected from the group consisting of cupric chloride, cuprous chloride, copper nitrate, copper sulphate, copper cyanide, copper thiocyanate, copper acetate, copper fluoride, copper bromide, copper methoxide and copper hydroxide.

7. A method according to claim 1, where the amount of copper compound catalyst is within a range of about 0.01 to 10 mole percent per mole of the silicon compound.

8. A method according to claim 1, where the amount of copper compound catalyst is within a range of about 0.01 to 5 mole percent per mole of the silicon compound.

9. A method according to claim 1, where the tertiary-hydrocarbylsilyl compound is (t-butyl)(n-propyl) dichlorosilane.

10. A method according to claim 1, where the tertiary-hydrocarbylsilyl compound is t-butyldimethylchlorosilane.

* * * * *